United States Patent
Hwang et al.

(10) Patent No.: US 8,986,986 B2
(45) Date of Patent: Mar. 24, 2015

(54) CELL LYSIS DEVICE AND METHODS OF LYSING CELLS OR VIRUSES

(75) Inventors: Kyu-youn Hwang, Yongin-si (KR);
Joon-ho Kim, Seongnam-si (KR);
Sung-hong Kwon, Yongin-si (KR);
Chin-sung Park, Yongin-si (KR);
Hee-kyun Lim, Hwaseong-si (KR);
Sun-ok Jung, Seongnam-si (KR);
Won-jong Jung, Seongnam-si (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 0 days.

(21) Appl. No.: 13/284,364

(22) Filed: Oct. 28, 2011

(65) Prior Publication Data
US 2012/0107912 A1    May 3, 2012

(30) Foreign Application Priority Data
Oct. 29, 2010 (KR) .................. 10-2010-0107014
Apr. 12, 2011 (KR) .................. 10-2011-0033867

(51) Int. Cl.
| C12M 1/33 | (2006.01) |
| C12M 3/08 | (2006.01) |
| C12Q 1/68 | (2006.01) |
| C12Q 1/70 | (2006.01) |
| C12M 3/00 | (2006.01) |
| C12M 1/00 | (2006.01) |

(52) U.S. Cl.
CPC .. *C12M 1/00* (2013.01); *C12M 1/33* (2013.01)
USPC ........... 435/306.1; 435/6.1; 435/5; 435/287.2

(58) Field of Classification Search
None
See application file for complete search history.

(56) References Cited

U.S. PATENT DOCUMENTS

| 6,168,948 B1* | 1/2001 | Anderson et al. ........... 435/287.2 |
| 6,440,725 B1* | 8/2002 | Pourahmadi et al. ...... 435/288.5 |
| 6,660,472 B1 | 12/2003 | Santoro et al. |
| 6,887,693 B2 | 5/2005 | McMillan et al. |
| 2002/0019060 A1 | 2/2002 | Petersen et al. |

(Continued)

FOREIGN PATENT DOCUMENTS

| CN | 101415813 A | 4/2009 |
| EP | 1 797 956 A1 | 6/2007 |

(Continued)

OTHER PUBLICATIONS

Kim et al., "Microfluidic sample preparation: cell lysis and nucleic acid purification," Integrative Biology, 1, pp. 574-586 (2009).*

(Continued)

*Primary Examiner* — Michelle S Horning
*Assistant Examiner* — M. Franco Salvoza
(74) *Attorney, Agent, or Firm* — Leydig, Voit & Mayer, Ltd.

(57) ABSTRACT

A method of lysing at least one of a cell and a virus, the method including: contacting a sample, which includes at least one of a cell and a virus, with a plurality of beads which are disposed in a first chamber to obtain a combination of the sample and the beads; and agitating the combination of the sample and the beads to lyse the at least one of the cell and the virus, wherein in the first chamber a liquid volume fraction is 0.6 or less, and wherein the liquid volume fraction is a value obtained by dividing a liquid volume of the first chamber by a pure void volume equivalent to a sum of the liquid volume of the first chamber and a void volume of the first chamber.

19 Claims, 6 Drawing Sheets

(56) References Cited

U.S. PATENT DOCUMENTS

| | | |
|---|---|---|
| 2002/0148992 A1 | 10/2002 | Hayenga et al. |
| 2003/0175947 A1 | 9/2003 | Liu et al. |
| 2008/0014122 A1 | 1/2008 | Kim et al. |
| 2008/0199930 A1 | 8/2008 | Lee et al. |
| 2010/0167384 A1 | 7/2010 | Clemmens et al. |

FOREIGN PATENT DOCUMENTS

| | | |
|---|---|---|
| JP | 2003-000226 A | 1/2003 |
| JP | 2006-141292 A | 6/2006 |
| WO | WO 03/015922 A1 | 2/2003 |
| WO | WO 03/015923 A1 | 2/2003 |
| WO | 2008/030631 A2 | 3/2008 |
| WO | WO 2008/104916 A2 | 9/2008 |

OTHER PUBLICATIONS

Culley et al., "Optimization of RNA isolation from the archaebacterium *Methanosarcina barkeri* and validation for oligonucleotide microarray analysis," Journal of Microbiological Methods 67, pp. 36-43 (2006).*

Hwang et al., Miniaturized bead-beating device to automate full DNA sample preparation processes for Gram-positive bacteria, *Lab Chip*, 2011, 11: 3649-3655.

Kido et al., "A novel, compact disk-like centrifugal microfluidics system for cell lysis and sample homogenization," *Collides and Surface B: Biointerfaces*, 2007, 58: 44-51.

Kim et al, "Cell lysis in a microfluidic CD (compact disk)," *Lab Chip*, 2004, 4: 516-522.

Lin et al., "Cell lysis methods for high-throughput screening or miniaturized assays," *Biotechnology Journal*, 2009, 4: 210-215.

Weibel et al., "Microfabrication meets microbiology," *Nature Reviews: Microbiology*, 2007, 5: 209-218.

Davis et al., "The Elastohydrodynamic Collision of Two Spheres," *J. Fluid Mech.*, 163: 479-497 (1986).

Kim et al., "Microfluidic Sample Preparation: Cell Lysis and Nucleic Acid Purification," *Integrative Biology*, 1: 574-586 (2009).

Schmeeckle et al., "Interparticle Collision of Natural Sediment Grains in Water," *Water Resources Research*, 37(9): 2377-2391 (2001).

Taylor et al., "Lysing Bacterial Spores by Sonication through a Flexible Interface in a Microfluidic System," *Analytical Chemistry*, 73(3): 492-496 (2001).

Chinese Office Action in Application No. 2011-10332898.9, issued Jun. 24, 2014.

Zhanglin et al., "Cell Lysis methods for high-throughput screening or miniaturized assays", *Biotechnology Journal*, vol. 4, No. 2, pp. 210-215 (2009).

* cited by examiner

SEQUENCE LISTING

<160> NUMBER OF SEQ ID NOS: 6

<210> SEQ ID NO 1
<211> LENGTH: 21
<212> TYPE: DNA
<213> ORGANISM: S.aureus

<400> SEQUENCE: 1
gttgcatcgg aaacattgtg t                                           21

<210> SEQ ID NO 2
<211> LENGTH: 27
<212> TYPE: DNA
<213> ORGANISM: S. aureus

<400> SEQUENCE: 2
atgaccagct tcggtactac taaagat                                     27

<210> SEQ ID NO 3
<211> LENGTH: 18
<212> TYPE: DNA
<213> ORGANISM: MRSA

<400> SEQUENCE: 3
acgagtagat gctcaata                                               18

<210> SEQ ID NO 4
<211> LENGTH: 19
<212> TYPE: DNA
<213> ORGANISM: MRSA

<400> SEQUENCE: 4
ggaataatga cgctatgat                                              19

<210> SEQ ID NO 5
<211> LENGTH: 20
<212> TYPE: DNA
<213> ORGANISM: Artificial Sequence
<220> FEATURE:
<223> OTHER INFORMATION: Taqman probe for S. aureus
<220> FEATURE:
<221> NAME/KEY: misc_feature
<222> LOCATION: (1)
<223> OTHER INFORMATION: 5' terminal is labelled with FAM
<220> FEATURE:
<221> NAME/KEY: misc_feature
<222> LOCATION: (20)
<223> OTHER INFORMATION: 3'-terminal is labelled with MGB-NFQ

<400> SEQUENCE: 5
tgtatgtaaa agccgtcttg                                             20

<210> SEQ ID NO 6
<211> LENGTH: 25
<212> TYPE: DNA
<213> ORGANISM: Artificial Sequence
<220> FEATURE:
<223> OTHER INFORMATION: Taqman probe for MRSA
<220> FEATURE:
<221> NAME/KEY: misc_feature
<222> LOCATION: (1)
<223> OTHER INFORMATION: 5'-terminal is labelled with FAM

```
<220> FEATURE:
<221> NAME/KEY: misc_feature
<222> LOCATION: (25)
<223> OTHER INFORMATION: 3'-terminal is labelled with BHQ1

<400> SEQUENCE: 6
ccaatctaac ttccacatac catct                                         25
```

CELL LYSIS DEVICE AND METHODS OF LYSING CELLS OR VIRUSES

CROSS-REFERENCE TO RELATED APPLICATIONS

This application claims priority to Korean Patent Application No. 10-2010-00107014, filed on Oct. 29, 2010, and Korean Patent Application No. 10-2011-0033867, filed on Apr. 12, 2011, and all the benefits accruing therefrom under 35 U.S.C. §119, the contents of which in their entirety are herein incorporated by reference.

BACKGROUND

1. Field

The present disclosure relates to cell lysis device and a method of lysing cells or viruses.

2. Description of the Related Art

Cell lysis, which is generally used in biological analysis, causes a release of cellular content. For example, analyzing nucleic acid in cells generally involves cell disruption to release the nucleic acid from the cell, and then analysis of the released nucleic acid.

Bead beating is a known method of cell lysis. The bead beating method disrupts cells in the presence of small beads with vigorous agitation. In a simple example of bead beating, cells and beads are mixed in a test tube with a vortex mixer to lyse the cells. The bead beating method can be performed with table top equipment.

Nonetheless, there remains a need for an efficient cell lysis method compatible within a microfluidic device.

SUMMARY

Provided is an efficient cell or virus lysis method using bead beating.

Additional aspects will be set forth in part in the description which follows and, in part, will be apparent from the description.

According to an aspect, a method of lysing at least one of a cell and a virus includes: contacting a sample, which includes at least one of a cell and a virus, with a plurality of beads which are disposed in a first chamber to obtain a combination of the sample and the beads; and agitating the combination of the sample and the beads to lyse the at least one of the cell and the virus, wherein, in the first chamber, a liquid volume fraction ($f_L$) is 0.6 or less, and wherein the liquid volume fraction ($f_L$) is a value obtained by dividing a liquid volume ($V_L$) of the first chamber by a pure void volume equivalent to a sum of the liquid volume ($V_L$) of the first chamber and a void volume ($V_O$) of the first chamber.

Also disclosed is a cell lysis device including: a first chamber fluidly connected to an net and an outlet, and a plurality of beads disposed in the first chamber, wherein a diameter of the beads is larger than a diameter of the net and the outlet; a second chamber including a port fluidly connected to the second chamber; and a flexible membrane sealably disposed between the first and second chambers.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
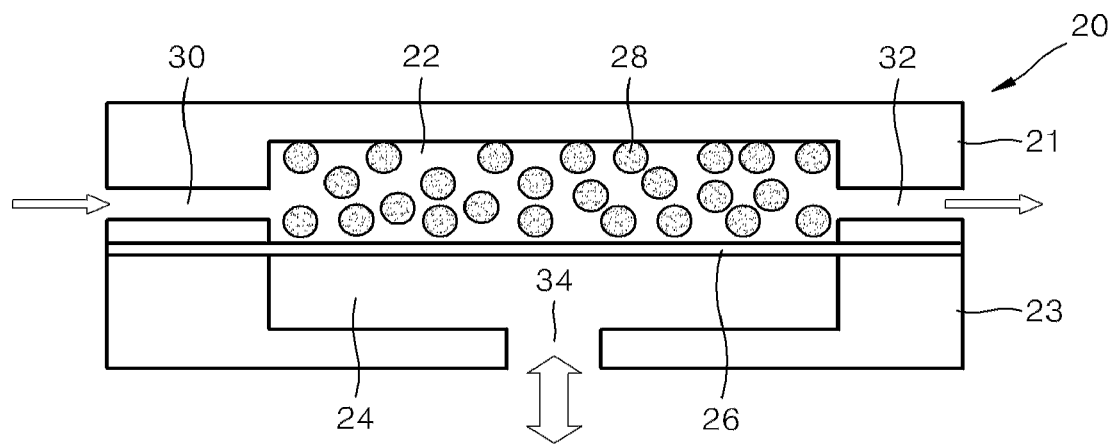
FIGS. 1 and 3 to 6 are cross-sectional views of an embodiment of a cell lysis device that may be used in an embodiment of a cell lysis method.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are further described below, by referring to the figures, to explain aspects of the present description.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms "first," "second," "third" etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first "element," "component," "region," "layer," or "section" discussed below could be termed a second element, component, region, layer or section without departing from the teachings herein.

The terminology used herein is for the purpose of describing particular embodiments only and is not intended to be limiting. As used herein, the singular forms "a," "an" and "the" are intended to include the plural forms as well, unless the context clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations)) and the spatially relative descriptors used herein interpreted accordingly.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present invention.

According to an aspect of the present disclosure, a method of lysing cells or viruses in a sample may include: contacting a sample, which comprises at least one of a cell and a virus, with a plurality of beads which are disposed (e.g. contained) in a first chamber to obtain a combination of the sample and the beads; and agitating the combination of the sample and the beads to lyse the at least one of the cell and the virus, wherein in the first chamber a liquid volume fraction ($f_L$) is 0.6 or less. The "liquid volume fraction ($f_L$)" is a value obtained by dividing a liquid volume ($V_L$) of the first chamber by a pure void volume equivalent to a sum of the liquid volume ($V_L$) and a void volume ($V_O$) of the first chamber.

The method of lysing may comprise contacting the sample, which comprises the at least one of cell and virus, with the beads, which are disposed in the first chamber.

The first chamber may provide a sealed or confined space. For example, the first chamber may be a chamber in a microfluidic device. The first chamber may have an Internal volume of about 1 μl to about 1000 μl, specifically about 1 μl to about 500 μl, more specifically about 1 μl to about 300 μl, or about 1 μl to about 200 μl, or about 1 μl to about 100 μl, or about 1 μl to about 50 μl, or about 10 μl to about 50 μl, or about 10 μl to about 40 μl, or about 20 μl to about 40 μl. The first chamber may have an inlet and an outlet. The inlet and outlet may be at the same location or different locations. At least one of the net and the outlet may be connected to (e.g., in fluid communication with) the first chamber through a flow path such as a channel. At least one of the net and outlet may have a diameter (e.g., a largest diameter) which is less than a diameter (e.g. a smallest diameter) of the beads to effectively block passage of the beads out of the first chamber. The flow path interconnecting at least one of the net and the outlet in fluid communication with the first chamber may have a region having a diameter (e.g., a smallest diameter) which is less than a diameter (e.g., a largest diameter) of the beads to effectively prevent the beads from exiting or being discharged from the first chamber through the flow path or flowing into the first chamber through the flow path. At least one of the inlet, the outlet, and the flow path may further include a weir to prevent the beads from passing out of it or inflowing thereinto. The at least one selected from inlet and outlet may have a valve or means for closing or opening the inlet and outlet so as to control fluid flow. Further, the flow path interconnecting at least one of the inlet and the outlet in fluid communication with the first chamber may have a valve or means for closing or opening the flow path so as to control fluid flow. Thus, when only one of the inlet and outlet has a diameter which is less than a diameter of the beads or which selected such that it blocks passage of the beads, the other one may be closed to prevent the beads passing out of the first chamber through the other one. Further, when only one of the inlet and outlet has a diameter which is less than a diameter of the beads or which selected such that it blocks passage of the beads, the direction of fluid flow may be controlled to prevent beads passing out the first chamber, i.e., the fluid may be controlled to flow from the inlet or outlet having a diameter which is more than a diameter of the beads to the other one having a diameter which less than a diameter of the beads.

The first chamber may be connected to a unit for agitating the combination of the sample and the beads, or may be formed to be able to agitate the combination of the sample and the beads in the first chamber. In an embodiment, the first chamber may be connected to an ultrasonic generator so that the beads in the first chamber may be agitated by ultrasonic waves. The first chamber may have a wall, at least a portion of which comprises a flexible membrane. In an embodiment, at least a portion of a wall of the first chamber may comprise the flexible membrane, which may form a portion of a second chamber. In other words, at least a portion of the first and second chambers may be defined in common by the flexible membrane. Also, the flexible membrane may be sealably disposed between the first and second chambers so that the flexible membrane is deformed according to a pressure of the second chamber. The second chamber may be connected to (e.g., fluidly connected to) a pressurizing unit and/or a depressurizing unit. The pressurizing unit and/or the depressurizing unit may be a pump, for example. In an embodiment the pump is a pneumatic pump. The second chamber may be alternately pressurized and depressurized such that the flexible membrane vibrates, thereby agitating the beads in the first chamber. The second chamber may also be connected (e.g., fluidly connected to or physically connected to) to an ultrasonic generator. The beads in the first chamber may be agitated as ultrasonic waves are applied to the flexible membrane by the ultrasonic generator. The flexible membrane may comprise an elastic material. The flexible membrane may have a thickness of from about 1 micrometer (μm) to about 5 mm, specifically about 0.025 mm to about 0.5 mm, more specifically about 0.03 mm to about 0.4 mm.

As used herein, the term "agitation" refers to inducing motion, e.g., motion of the beads. The agitation may be induced by applying a form of energy to the combination of the sample and the beads, and may comprise inducing a form of bead beating. The bead beating may comprise, for example, bead-to-bead beating (e.g., bead to bead contact), bead-to-liquid-medium beating, bead-to-wall beating, or bead-to-cell or virus beating. A cell or virus in the sample may be lysed by such agitation. The lysis may occur by mechanical beating, a shear force, or the like, but is not limited to a specific mechanism. Hereinafter, lysing of a cell and/or virus by agitating the combination of the sample and the beads may be referred to as a bead beating method, and in an embodiment is a bead beating method. The agitation may be performed with the first chamber sealed or not sealed.

The beads may be rigid enough to be used as a cell lyses media. Beads, as used herein, refer to spherical bodies or non-spherical bodies, and can have any shape so long as the shape does not adversely affect the desirable features of the disclosed method or device. The beads may comprise a solid material, and in an embodiment, may be coated with a solid material. In an embodiment the beads are a solid particle. In another embodiment the beads are hollow. The beads may be magnetic or non-magnetic. The beads may comprise at least one of a glass, metal, and metal oxide. In an embodiment, the beads comprise at least one of glass beads, metal beads, and metal oxide beads. The metal oxide may comprise at least one of $ZrO_2$, $SO_2$, $Al_2O_3$, $Fe_2O_3$, and $TiO_2$. In an embodiment, the beads comprise a combination of, for example, $ZrO_2$ and $SO_2$. The metal beads may comprise, for example, steel beads or stainless steel beads. Glass beads are specifically mentioned.

The beads are not limited to microscale dimensions, and may have any dimensions so long as a cell can be lysed by the operation of the cell lysis device. For example, the smallest dimension of the beads may be from about 10 nanometers (nm) to about 1000 μm, specifically about 10 nm to about 700 μm, more specifically about 10 nm to about 500 μm, or about 10 nm to about 300 μm, or about 10 nm to about 100 μm, or about 10 nm to about 50 μm, or about 10 nm to about 10 μm in size, and in an embodiment, may be from about 50 nm to about 1000 μm, specifically about 50 nm to about 900 μm, more specifically about 50 nm to about 700 μm, or about 50 nm to about 500 μm, or about 50 nm to about 300 μm, or about 50 nm to about 100 μm, or about 50 nm to about 50 μm, or about 50 nm to about 10 μm in size, and in another embodiment, may be from about 100 nm to about 1000 μm, specifically about 100 nm to about 900 μm, more specifically about 100 nm to about 700 μm, or about 100 nm to about 500 μm, or about 100 nm to about 300 μm, or about 100 nm to about 100 μm, or about 100 nm to about 50 μm, or about 100 nm to about 10 μm, and in yet another embodiment, may be from about 1 μm to about 500 μm, specifically about 1 μm to about 300 μm, more specifically about 1 μm to about 100 μm, or about 1 μm to about 50 μm, or about 1 μm to about 30 μm, or about 1 μm to about 10 μm in size. The beads may be at least one of spherical, planar, or multi-planar. The beads in the first chamber may be at least one, for example two in number. In an embodiment, the number of beads in the first chamber may be 10 or greater, specifically 100 or greater, more specifically 1000 or greater, or 10,000 or greater, or 100,000 or greater, or $10^8$ or greater. For example, the number of beads in the first chamber may be from about 1 to about $10^8$, specifically about 100 to about $10^6$. The first chamber may be manufactured such that the beads are placed in a space and blocked by the first chamber, so that the beads may be unable to pass out of an inlet or an outlet. A density D of the beads in the first chamber may be greater than or equal to 1 gram per cubic centimeter ($g/cm^3$), specifically about 1 $g/cm^3$ to about 20 $g/cm^3$, more specifically about 1 $g/cm^3$ to about 15 $g/cm^3$, or about 1 $g/cm^3$ to about 10 $g/cm^3$, or about 1 $g/cm^3$ to about 8 $g/cm^3$, or about 1 $g/cm^3$ to about 6 $g/cm^3$, or about 1 $g/cm^3$ to about 4 $g/cm^3$, or about 3 $g/cm^3$ to about 20 $g/cm^3$, or about 3 $g/cm^3$ to about 15 $g/cm^3$, or about 3 $g/cm^3$ to about 10 $g/cm^3$, or about 3 $g/cm^3$ to about 8 $g/cm^3$, or about 3 $g/cm^3$ to about 6 $g/cm^3$, or about 3 $g/cm^3$ to about 4 $g/cm^3$.

At least one of a wall of the first chamber and a surface of the beads may comprise a binding material which is able to bind to a cell or virus, and in an embodiment, may be coated with the binding material. The binding material may be a material which specifically binds to the cell or virus. The specific binding material may be at least one of an antibody for an antigen, a substrate or inhibitor for an enzyme, an enzyme for a substrate, a receptor for a ligand, and a ligand for a receptor. The binding material may be a material which non-specifically binds to the cell or virus. The non-specific binding material may be a hydrophobic material having a water contact angle of about 70° to about 95°, and in an embodiment, may include a material with at least one amino group. The material with at least one amino group may include a polymer having at least two amino groups. The material with at least one amino group may include polyethyleneimine ("PEI"). The hydrophobic material with a water contact angle of about 70° to about 95° may include octadecyldimethyl(3-trimethoxysilyl propyl)ammonium ("OTC") or tridecafluorotetrahydrooctyltrimethoxylsilane ("DFS"). The wall of the first chamber or the surface of the beads comprising the binding material may be of use in capturing or adsorbing the cell or virus to separate them.

In the contacting of the sample and the beads, the sample may comprise at least one of the cell and the virus. The sample may be a biological sample, wherein "biological sample" refers to a sample comprising an organism or a derivative thereof. A biological sample can be isolated from an individual, e.g., a tissue sample or a biological fluid, or isolated from the environment, such as from a body of water, from the soil, or from a food source or an industrial source. The individual can be an animal such as a human. Examples of a biological sample include saliva, sputum, blood, blood cells (such as leukocytes and erythrocytes), amniotic fluid, serum, semen, bone marrow, a tissue or a microneedle biopsy specimen, urine, a peritoneal fluid, a pleural fluid, and cell cultures. Further, examples of the biological sample include a tissue slice, such as a frozen tissue slice for a histological purpose. In an embodiment, the biological sample is blood, urine, or saliva, for example. The cell may be a prokaryote or a eukaryote. The prokaryote may be a bacterial cell, and may be gram-negative or gram-positive. The eukaryote may comprise at least one of a plant cell, animal cell, or fungal cell. The cell or virus may be contained in an appropriate liquid medium. The liquid medium may comprise at least one of, for example, a cell culture medium, a buffer (for example, a phosphate-buffered saline ("PBS") solution), saline, and water. The liquid medium may be a cell lysis solution. The cell lysis solution may be additionally supplied into the first chamber following the contacting of the sample and, beads, which may be contained in a liquid medium which comprises the cell, and in an embodiment, may be combined with the liquid medium and then be supplied into the first chamber. The cell lysis solution may comprise a non-specific cell lysis agent or a specific cell lysis agent. The non-specific cell lysis agent may comprise at least one of a surfactant, NaOH, and a chaotropic salt. The specific cell lysis agent may comprise at least one of a lysozyme, lysostaphin, penicillin, and a β-lactam antibiotic, for example.

The contacting of the sample and the beads may be achieved by applying a positive pressure to the inlet of the chamber or by applying a negative pressure to the outlet, thereby introducing the sample to the chamber. The negative pressure or positive pressure may be applied using, for example, a pump. The pump may be at least one of a peristaltic pump and a pneumatic pump, for example. The cell or virus may be introduced by direct injection by a user. In an embodiment, the cell or virus may be injected by pipetting by a user. The flow rate or amount of the sample may be selected depending on at least one of the type of cell or virus to be lysed, the purpose of cell lysis, and any process following the cell lysis, if present, and the details of the foregoing may be determined by one of ordinary skill in the art without undue experimentation.

The contacting of the sample and the beads may comprise flowing the sample into the inlet of the first chamber and a portion of the sample may be discharged through the outlet of the first chamber. The sample may be introduced to the first chamber at a flow rate of about 10 μl/min to about 1000 μl/min, specifically about 100 μl/min to about 500 μl/min.

The method of lysing may comprise agitating the combination of the sample and the beads to lyse the cell and/or virus. The agitating may be induced by ultrasonic waves or wall vibration of the first chamber. In an embodiment, a portion of a wall forming a portion of the first chamber, which may comprise a flexible membrane, may be pressurized and then depressurized, or vice versa to vibrate the flexible membrane, thereby agitating the combination of the sample and the beads. The flexible membrane may be vibrated at a frequency of about 0.001 Hertz (Hz) to about 100 kilohertz (kHz), specifically about 0.01 Hz to about 100 kHz, more specifically at a frequency of about 0.1 Hz to about 100 kHz, or a frequency of about 1 Hz to about 100 kHz, or a frequency of about 5 Hz to about 100 kHz, or a frequency of about 10 Hz to about 100 kHz. The pressurizing may be performed using a tool connected to, e.g., physically connected to or fluidly connected to, at least one of the inlet and the outlet to provide a dynamic force to cause inflow and discharge of a fluid. The dynamic force providing tool may be any device able to induce motion of fluid, and in an embodiment, may be a device able to apply a positive pressure or a negative pressure to the first chamber, such as a pump. The pump may be a micropump implementable in a microfluidic device. The micropump may be a mechanical or non-mechanical device. A mechanical microfluidic pump may in general include an actuator and a moving part, which may be a membrane or a flap, for example.

Driving power of the mechanical microfluidic pump may be generated using piezoelectric, electrostatic, thermo-pneumatic, pneumatic, or magnetic effects. A non-mechanical pump may function by generation of electro-hydrodynamic, electro-osmotic, or ultrasonic flow.

The inlet and outlet may be connected to and in fluid communication with the first chamber, for example, through a microchannel. The microchannel may have a width of about 1 micrometer (μm) to about 10 millimeter (mm), specifically a width of about 1 μm to about 1 mm, more specifically a width of about 1 μm to about 500 μm. The width may be a dimension in a direction perpendicular to a direction of flow in the cell lysis device, and may be parallel to a surface of the membrane 26.

In the method of lysing, a liquid volume fraction ($f_L$) in the first chamber, which contains the beads and the sample, may be 0.6 or less, specifically about 0.25 to about 0.6, more specifically about 0.3 to about 0.5. In an embodiment, the liquid volume fraction ($f_L$) may be zero. The "liquid volume fraction ($f_L$)" is a value obtained by dividing a liquid volume ($V_L$) of the first chamber by a pure void volume equivalent to a sum of the liquid volume ($V_L$) and a void volume ($V_O$) of the first chamber. The cell and/or virus in the sample may be lysed in a substantially moisture-free or dry condition. While not wanting to be bound by theory, alysis efficiency of the cell and/or virus was found to be remarkably high at a liquid volume fraction ($f_L$) of 0.6 or less.

The method of lysing may further comprise removing at least portion of the liquid in the first chamber, e.g., to reduce the liquid volume before the agitating and after the contacting of the sample and the beads. The reducing of the liquid volume may comprise drying the interior of the first chamber. The drying may comprise flowing a gas, for example air, into the first chamber, or by applying heat to the first chamber.

The method of lysing may further comprise washing the wall of the first chamber or the surface of the beads after the contacting of the sample and the beads, e.g., to remove an impurity remaining thereon unbound. The washing may be performed with a liquid medium which does not interfere with the binding of the cell and/or the virus. The liquid medium may be a buffer such as phosphate buffered saline ("PBS"), or water, such as distilled water. The agitating may be performed after the washing.

The method may further comprise drying the wall of the first chamber or the surface of the beads after the washing. The agitating may be performed after the drying. The agitating may be performed when the liquid volume fraction has reached substantially zero, e.g., after the drying. The drying may be performed by flowing a gas, for example air, into the first chamber or by applying heat to the first chamber.

The method of lysing may further include introducing a cell or virus lysis solution into the first chamber. The cell or virus lysis solution may comprise at least one of NaOH, KOH, a chaotrope, and a surfactant. The cell or virus lysis solution may be introduced after the drying. The agitating may be performed after the introducing of the cell or virus lysis solution.

In the method of lysing, the method may be performed in a cell lysis device, and the cell lysis device may comprise a first chamber, a second chamber, and a flexible membrane disposed between the first and second chambers, wherein the second chamber is a pressurizing and depressurizing chamber, which is suitable for vibrating the flexible membrane between the first and second chambers.

FIG. 1 is a sectional view of an embodiment of a cell lysis device 20. The cell lysis device 20 may be used in the above-disclosed method of lysing. Referring to FIG. 1, the cell lysis device 20 includes an upper plate 21, a lower plate 23, and a membrane 26. The membrane 26 is disposed between the upper plate 21 and the lower plate 23. A spatial region of the upper plate 21 defines a first chamber 22, and a spatial region of the lower plate 23 defines a second chamber 24. The first and second chambers 22 and 24 are separated by the membrane 26 disposed therebetween. In other words, the first chamber 22 is a space defined by the upper plate 21 and the membrane 26, and the second chamber 24 is a space defined by the lower plate 23 and the membrane 26.

The membrane 26 may be flexible. The membrane 26 may comprise a polymer membrane, such as a polydimethylsiloxane ("PDMS") membrane. In an embodiment, the membrane 26 is a PDMS membrane. The membrane 26 may have a thickness of, for example, from about 1 μm to about 5 mm, specifically about 10 μm to about 1 mm. The first chamber 22 may contain a plurality of beads 28 for cell lysis. In an embodiment, the beads for cell lysis may be beads 28, as illustrated in FIG. 1. Since the first chamber 22 is defined by the membrane 26, the beads 28 in the first chamber 22 may contact the membrane 28. The beads 28 may be microbeads. The beads 28 are an example of micro units, e.g., particles, for lysing cells, and thus, other units may be used in place of the beads 28. The beads 28 may have a diameter, e.g., an average largest diameter of, for example, from about 1 μm to about 500 μm, specifically 10 μm to about 400 μm, more specifically 20 μm to about 300 μm. A density D of the beads 28 in the first chamber 22 may be greater than or equal to 1 g/cm$^3$, and in an embodiment, may be from about 1 g/cm$^3$ to about 20 g/cm$^3$, specifically 2 g/cm$^3$ to about 15 g/cm$^3$, more specifically 4 g/cm$^3$ to about 10 g/cm$^3$. More than one bead may be included in the liquid medium, and in an embodiment, there may be 10, 100, 1000, 10000, or 10$^9$ or greater beads per 1 μl of the liquid medium. The micro units in the first chamber may be in number about 1 to about 10$^8$ per 1 μl of the liquid medium, and in another embodiment, may be from about 100 to about 10$^6$ per μl. The beads 28 may comprise at least one of a glass, a metal, or a metal oxide. In an embodiment, the beads are glass beads. In another embodiment, the beads 28 may be metal oxide beads or metallic beads. The metal oxide may comprise at least one of $ZrO_2$, $SiO_2$, $Al_2O_3$, $Fe_2O_3$, and $TiO_2$. The metal oxide may be, for example, a combination of $ZrO_2$ and $SiO_2$. The metallic beads may be, for example, steel beads or stainless steel beads. If the beads 28 comprise a composition of a glass or a metal oxide, a surface modification for cell capture or adsorption may be facilitated.

The cell lysis device 20 includes an inlet 30 and an outlet 32. The inlet 30 and the outlet 32 may have a diameter smaller than that of the beads 28. A solution comprising a cell to be disrupted is introduced into the first chamber 22 through the inlet 30. The resulting product of disruption of cell membranes and/or walls, including a nucleic acid and the like, is released through the outlet 32. The inlet 30 penetrates a first wall of the upper plate 21 to fluidly connect with a first side of the first chamber 22. The outlet 32 penetrates a second wall of the upper plate 21 to fluidly connect with a second &de, e.g., an opposite second side, of the first chamber 22.

The second chamber 24 may be a pneumatic chamber including a space into which a fluid, such as air, pressing periodically or non-periodically on the membrane 26, is introduced. High-pressure fluid is introduced into the second chamber 24, thereby pressing the membrane 26. When pressed, the membrane 26 may protrude toward the first chamber 22, thereby reducing the spatial volume of the first chamber 22. Alternatively, when depressed, the membrane 26 may deflect down towards the second chamber 24. The second chamber 24 may have a port 34 as an inflow and outflow passage of a fluid which pressurizes the interior of the second chamber 24. As the fluid is periodically or non-periodically introduced into or released from the second chamber 24 through the port 34, the membrane 26 may periodically or non-periodically vibrate. The vibration of the membrane 26 may eventually periodically or non-periodically pressurize the beads 28 in the first chamber 22 by direct contact with the beads 28 or via the solution in the first chamber 22. As a result, the beads 28 are induced to move, thus colliding against each other or against an inner wall of the first chamber 22 due to the motion. Due to the motion of the beads 28, the cell introduced into the interior of the first chamber 22 is disrupted by being sheared or ground. The pressurizing or depressurizing of the interior of the second chamber 24 by the supply or release of the fluid into or out of the second chamber 24 may be selected with respect to the number of vibrations of the membrane 26, and may be from about 0.001 Hz to about 100 kHz, specifically about 0.01 Hz to about 10 kHz, more specifically about 0.1 Hz to about 1 kHz.

Figure 2:
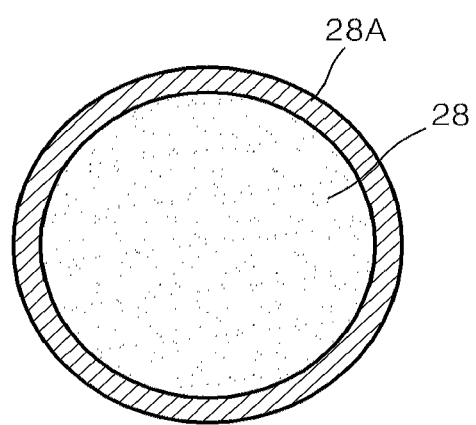
FIG. 2 is a sectional view of an embodiment of a bead comprising a cell capturing organic layer on its surface.

The beads 28 may have an organic layer 28A on a surface thereof, as illustrated in FIG. 2, for specific or non-specific cell capture. For example, to selectively capture a specific cell, an antibody, an aptamer, or the like may be coated on the surface of the beads 28. A non-specific cell may be captured by the action of a hydrophobic or electrostatic force.

The organic layer 28A may be formed by modifying the surfaces of the beads 28 in various ways using organosilane. A bead having an organosilane modified surface is specifically mentioned.

When the surfaces of the beads 28 have a unit with a specific or non-specific affinity to the cell, the cell introduced into the first chamber 22 may be captured by the beads 28. In this state, the vibration of the membrane 26 may cause the beads 28 to move, and thus, to collide against each other or the inner wall of the first chamber 22. During this process, the cells captured by the beads 28 may be disrupted.

In an embodiment, after supplying the solution containing the cell to be disrupted into the first chamber 22, a substance with an enhanced cell lysis effect may be supplied into the first chamber 22, followed by cell disruption. The substance may be a cell lysis solution. The cell lysis solution may comprise, for example, at least one of NaOH, KOH, a chaotrope solution, a surfactant, or the like. The cell lysis solution may be used in a concentration which does not adversely affect a post-process following the cell disruption, such as a polymerase chain reaction ("PCR") process, so that the PCR may be conducted immediately after the cell disruption without an additional purification. If the substance is used in a concentration affecting PCR, an additional purification may be carried out. The cell lysis solution may be supplied after the cell disruption to facilitate the release of nucleic acid.

In an embodiment, after the supply of the solution containing the cell to be disrupted into the first chamber 22, cell disruption may be carried out without additional supply of the cell lysis solution into the first chamber 22.

Figure 3:
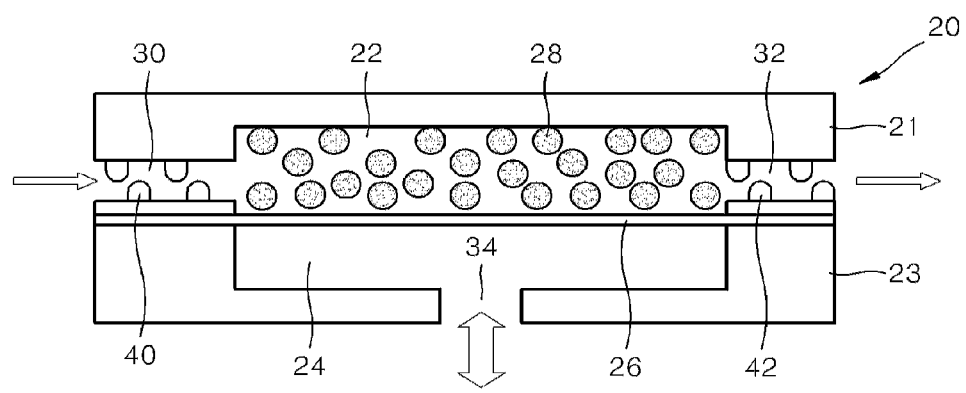

FIG. 3 illustrates an alternative embodiment of the cell lysis device 20. Described hereinafter are only the portions not identical with those of the cell lysis device 20 of FIG. 1. This also applies to FIGS. 5-8.

Referring to FIG. 3, the inlet 30 and the outlet 32 may have a diameter, e.g., a smallest diameter, which is larger than a diameter, e.g., a largest diameter, of the beads 28. A plurality of first protrusions 40 may be distributed on an inner side of the inlet 30. The plurality of first protrusions 40 may be evenly distributed throughout the inner side of the inlet 30. The plurality of first protrusions 40 may be disposed to protrude in opposite directions. Due to the first protrusions 40, an actual diameter or effective diameter of the inlet 30 may be smaller than the diameter, e.g., a smallest diameter, of the beads 28. A plurality of second protrusions 42 may be distributed on an inner side of the outlet 32. The distribution of the second protrusions 42 may be identical with that of the first protrusions 40. Due to the second protrusions 42, an actual diameter or effective diameter of the outlet 32 may be smaller than the diameter, e.g., smallest diameter, of the beads 28. The first protrusions 40 and the second protrusions 42 may be identical or different in shape. Alternatively, instead of the first and second protrusions 40 and 42, the inlet 30 and the outlet 32 may have an embossed inner surface.

Figure 4:
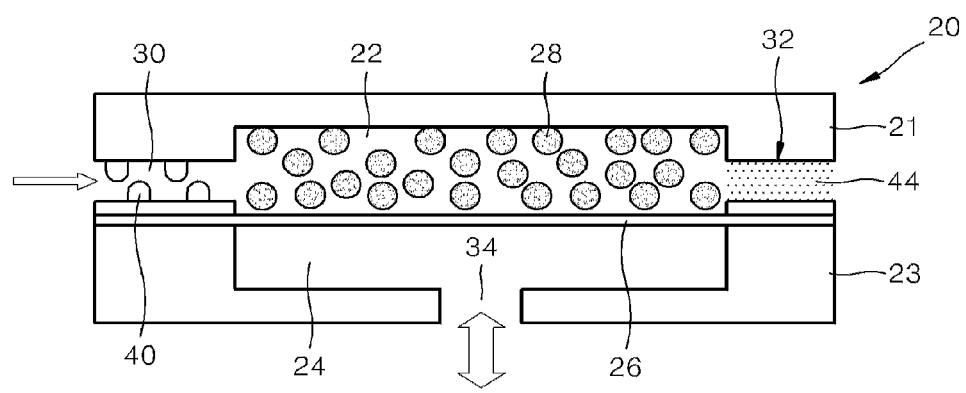

FIG. 4 illustrates another alternative embodiment of the cell lysis device 20.

Referring to FIG. 4, a filter 44 may be disposed in the outlet 32. The filter 44 may be a porous material that allows the contents of the disrupted cells to pass. The inlet 30 may have a diameter smaller than a diameter, e.g., a smallest diameter, of the beads 28, as in FIG. 1. Structural characteristics of the inlet 30 may be otherwise identical with those disclosed with respect to FIG. 3.

Figure 5:
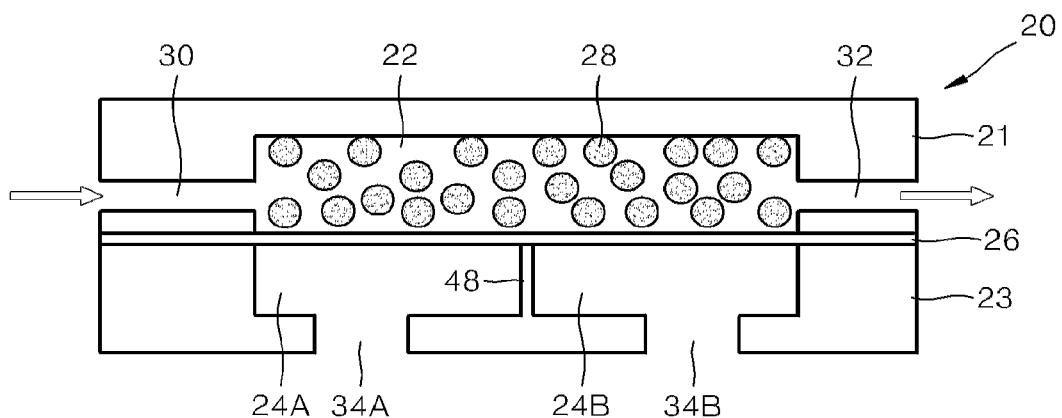

FIG. 5 illustrates another alternative embodiment of the cell lysis device 20.

Referring to FIG. 5, two chambers, i.e., a third chamber 24A and a fourth chamber 24B, may be provided instead of the second chamber 24 of FIG. 1. The third chamber 24A and the fourth chamber 24B may be separated by a partition wall 48. The role, e.g., function, of the third and fourth chambers 24A and 24B may be similar to that of the second chamber 24 of FIG. 1. The third chamber 24A may include a first port 34A, and the fourth chamber 24B may include a second port 34B. The role, e.g., function, of the first and second ports 34A and 34B may be similar to that of the port 34 of the second chamber 24. Structural characteristics of the inlet 30 and the outlet 32 may be identical with those described in relation with FIG. 3 or FIG. 4. A pressure may be applied simultaneously or sequentially to the first and second ports 34A and 34B to simultaneously or sequentially vibrate portions of the membrane 26 defining the third and fourth chambers 24A and 24B. A pressure with a same or different phase may be applied to the first and second ports 34A and 34B to vibrate the membrane 26 in each chamber in a same or different phase. For example, a positive pressure may be applied to the first port 34A, while a negative pressure may be applied to the second port 34B to vibrate the membrane 26 in the third chamber 24A and the membrane 26 in the fourth chamber 24B in opposite phases.

Figure 6:
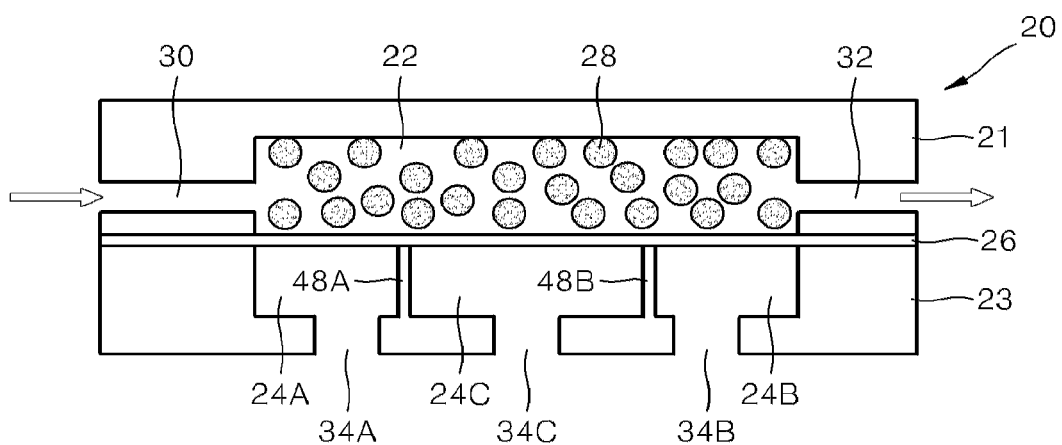

FIG. 6 illustrates another alternative embodiment of the cell lysis device 20.

Referring to FIG. 6, three chambers, i.e., third, fourth, and fifth chambers 24A, 24B, and 24C may be provided instead of the second chamber 24 of FIG. 1. The role, e.g., function, of the third, fourth, and fifth chambers 24A, 24B, and 24C may be similar to that of the second chamber 24 of FIG. 1. The third and fifth chambers 24A and 24C may be separated by a first partition wall 48A. The fourth and fifth chambers 24B and 24C may be separated by a second partition wall 48B. The third, fourth, and fifth chambers 24A, 24B, and 24C may have first, second, and third ports 34A, 34B, and 34C, respectively. The role, e.g., function, of the first, second, and third ports 34A, 34B, and 34C may be similar to that of the port 34 of the second chamber 24. Although the embodiment of FIG. 6 illustrates the division of the second chamber 24 of FIG. 1 into three chambers, in yet another embodiment the second chamber 24 of FIG. 1 may be divided into more than three chambers. A pressure may be applied simultaneously or sequentially to the first, second, and third ports 34A, 34B, and 34C to simultaneously or sequentially vibrate the membrane 26 defining each chamber. A pressure with a same or different phase may be applied to the first, second, and third ports 34A, 34B, and 34C to vibrate the membrane 26 in each chamber in a same or different phase. For example, a positive pressure may be applied to the first and third ports 34A and 34C, while a negative pressure is applied to the second port 34B to vibrate the membrane 26 in the third and fifth chambers 24A and 24C and the membrane 26 in the fourth chamber 24B in opposite phases.

The roles, e.g., functions, of the first and second chambers 22 and 24 in FIGS. 1 and 3 to 6 may be reversed. That is, either one of the first and second chambers 22 and 24 may contain beads 28, and the other chamber may be used as a chamber into which a fluid for pressurization is introduced. If the second chamber 24 is used as a chamber into which a fluid for pressurization is introduced, the port 34 of the second chamber 24 may be connected, e.g., fluidly connected, to a pressure controller (not shown) that is able to pressurize or depressurize the interior of the second chamber 24. The same applies to the third, fourth, and fifth chambers 24A, 24B, and 24C.

According to an aspect, provided a method of efficiently lysing a cell or virus using beat beating.

The disclosed embodiments will be described in further detail with reference to the following examples. These examples are for illustrative purposes only and shall not limit the scope of the invention.

EXAMPLE 1

Cell Lysis Effect with Respect to Liquid Volume Fraction

1. Manufacture of Cell or Virus Lysis Device

A cell or virus lysis device may be manufactured by disposing a commercially available elastic membrane between two glass chips. Chambers or channels may be defined using an entirety of a glass chip or a portion of the glass chips, which may then be combined with the elastic membrane therebetween, thereby completing the manufacture of the cell or virus lysis device.

In the current example, first and second glass chips were manufactured by defining channels and chambers in a glass wafer by photolithography, etching, and wet-etching processes, which are well known and the details of which can be determined without undue experimentation. After having been cleaned with a Piranha solution (i.e., a combination of sulfuric acid and hydrogen peroxide), a 6-inch glass wafer (borosilicate, 700 µm thick) was deposited with a 500 nanometer (nm) thick amorphous silicon layer by low-pressure chemical vapor deposition ("LPCVD"). Then, a patterning process was performed on a portion of the deposited silicon layer exposed through a photoresist film. The exposed part of the silicon layer was removed by dry etching. Afterwards, the photoresist film was stripped off, and the exposed glass wafer was wet-etched with a hydrofluoric acid solution (HF, 49%) to form a channel having a depth of about 100 µm and a width of about 200 µm. In the etching process for forming the channel, a weir (protrusion) projecting about 20 µm toward an inner center from an inner surface of the channel was formed to confine beads. The weft was formed to serve both as a valve seat and a bead trapping weft.

Then, after the silicon layer was removed, a dry film resist ("CFR") was coated and patterned. Then, a chamber including beads (ca. about 15.5 µl) and holes for fluid inflow or outflow were formed using a sand-blasting method. Subsequently, the glass wafer was diced into chip-shaped pieces, which were then washed with plasma. A fluidic chip ("first glass chip") including the above-manufactured chamber to contain the beads, and a pneumatic chip ("second glass chip") including a chamber to function as a pneumatic pump and not containing beads were permanently coupled with a 254 µm thick PDMS layer (available from Rogers Corporation) which was activated with a plasma between the first and second glass chips as an intermediate layer. The PDMS layer, which is a monolithic flexible layer, was used to control fluid flow and used as a pump and a valve and as an actuator for inducing collisions between the beads by pneumatic vibration.

About 15-16 milligrams (mg) (about $2 \times 10^5$ in number) surface-modified glass beads were put into the bead chamber, which was then sealed using a PCR-compatible adhesive tape (available from Applied biosystems). The attached tape was covered with a polycarbonate plate to prevent the tape from bending during operation such as a DNA extraction.

Operation of the PDMS layer was controlled by applying a positive pressure or a negative pressure to the pneumatic chamber with a Solenoid valve array (S070-5DC, available from SMC) connected thereto. The valves were coupled to an electro-pneumatic-regulator (ITV0030-3BL, available from SMC) and LabVIEW software (available from National Instruments). Operation of the valves associated with fluid transfer was visualized through an interface of the LabVIEW software in each step to monitor extraction of nucleic acids.

Figure 7:
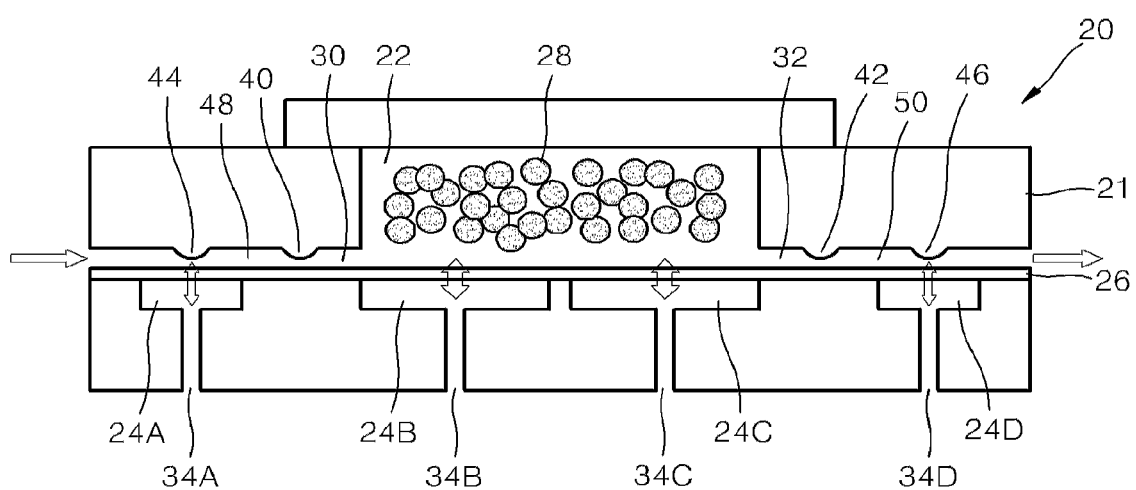
FIGS. 7 and 8 illustrate an embodiment of a cell lysis device, which may be used in an embodiment of a method of cell lysis.
Figure 8:
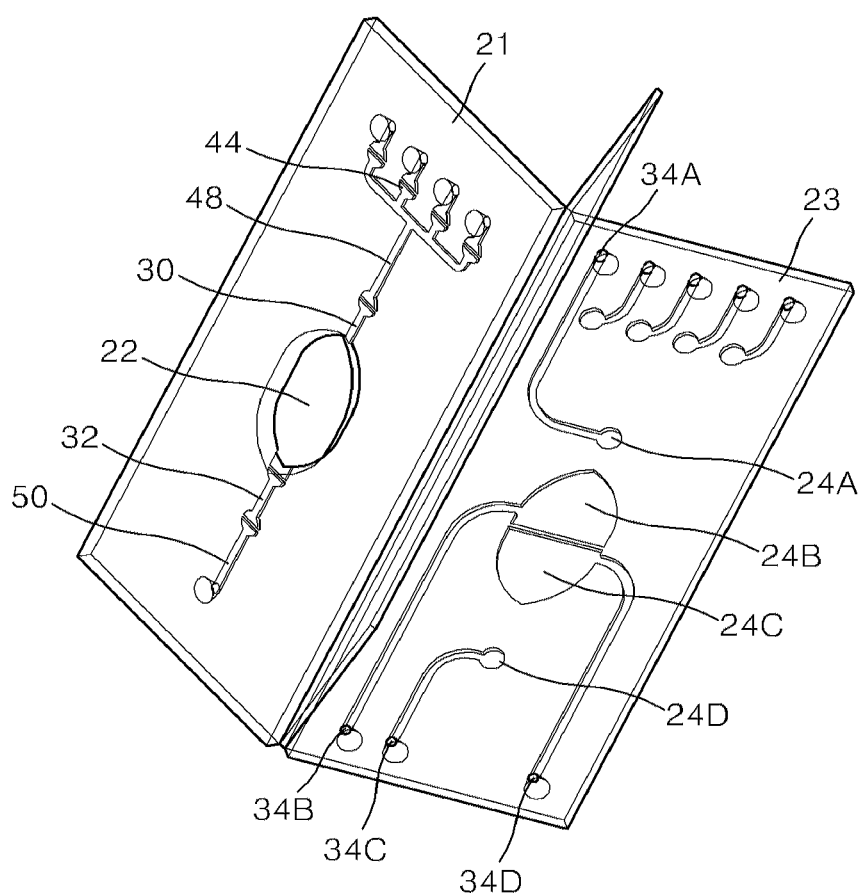

FIGS. 7 and 8 illustrate a cell lysis device used in the current Example. FIG. 7 is a cross-sectional view of the cell lysis device using bead beating in which collisions of beads are induced by the vibration of a PDMS layer. Referring to FIG. 7, an inlet with a first protrusion 40 and an outlet with a second protrusion 42 are connected to an inlet port and an outlet port, respectively, via fluid channels 48 and 50. First and second valve sheets 46A and 46B are formed on an upper plate, which defines the inlet and the outlet to correspond to the inlet and outlet ports, respectively. Pneumatic chambers, specifically first to fourth chambers 24A to 24D, are disposed in a lower plate and the first and the fourth chambers 24A and 24D correspond to the first and second valve sheats 44 and 46, respectively. First to fourth ports 34A to 34D are fluidly connected to the first to fourth chambers 24A to 24D.

FIG. 8 is an enlarged view of a 3-layered cell lysis device including monolithic Mass, PDMS and glass, and fluidic and pneumatic components of the cell lysis device.

2. Glass Bead Modification

After having been washed with a Piranha solution and then with distilled water, glass beads having a diameter of about 30 μm to 50 μm (available from Polysciences, Inc.) were filtered and vacuum-dried.

Afterwards, a 5% (volume/volume) trimethoxysilylpropyl-modified PEI ((poly(ethyleneimine)-trimethoxysilylpropyl: PEIM) solution (available from Gelest, Inc.) in ethanol was prepared as a bead-surface modification solution. The beads were put into the bead-surface modification solution and reacted for about 2 hours by gentle mixing, followed by filtration and washing with fresh ethanol three times. The final recovered glass beads were incubated in a 110° C. oven for 50 minutes, to obtain glass beads having surfaces coated with PEIM. PEIM is known to be able to non-specifically bind to cells, and thus the glass beads coated with the PEIM may be used to non-specifically separate cells.

3. Nucleic Acid Extraction

A 1 mL sodium acetate buffer (50 millimolar (mM), pH 4, available from Sigma-Aldrich) containing $10^6$ colony-forming units per milliliter (CFU/mL) of a sample S. aureus or Methicillin-resistant Staphylococcus aureus ("MRSA"), a 0.5-mL tris(hydroxymethyl)aminomethane ("Tris")-ethylenediaminetetraacetic acid ("EDTA") ("TE") buffer (10 mM Tris, 1 mM EDTA, pH 8.0, available from Ambion) for washing, and a 10 μl or 20 μl NaOH (0.02 normal (N), available from Sigma-Aldrich) for lysis were stored into a liquid reservoir beforehand. The liquid solution was transferred by a pressure-driven operation. An operating liquid pressure was determined through a preliminary test. Initially, while applying a pressure of 150 kiloPascals (kPa) from above the PDMS layer, the sample solution was directed through the chamber containing the beads at 30 kPa and at about 200 μl/minute. After flowing through the chamber, the solution was recovered to evaluate a cell capture efficiency. After the initial loading of the sample, the washing solution was directed through the chamber containing the beads at about 500 μl/min (80 kPa) to wash it, which was then air-dried at about 100 kPa for about 30 seconds. To lyse the captured cells, 6 ul of the lysis solution (0.02 N NaOH) was injected into the chamber containing the beads, and valves on opposite sides of the chamber were closed. Subsequently, pressures of two pneumatic chambers were adjusted to about 80 kPa and about −80 kPa, respectively, by an adjustment of a Solenoid valve controlled via a Labview program, to vibrate the PDMS layer at a frequency of about 10 Hz for about 5 minutes, thereby performing a cell lysis process. After the cell lysis process, with the inlet and the outlet opened, 4 μl or 14 μl of the NaOH solution was injected with an application of a fluid pressure of about 100 kPa, to recover alysed cell product through the outlet. The resulting lysed cell product containing a nucleic acid was 10 μl or 20 μl in total. The overall process took about 20 minutes or less. No additional DNA purification was performed.

Experiments with a positive lysis control ("PLC") and a negative lysis control ("NLC") were conducted as follows.

The experiment with a PLC was conducted using two different top bench lysis methods: an enzymatic method and a bead beating method. Two 1 mL sample solutions containing $10^4$ CFU/mL and $10^6$ CFU/mL of S. aureus were centrifuged in microcentrifuge tubes at about 13,200 revolutions per minute (rpm) for about 20 minutes to precipitate cells. Then, the supernatant was removed from each centrifuged product. The precipitated pellets were treated using the two methods. In the enzymatic method, after an incubation of the cell pellets with a lysostaphin solution (200 milligrams per milliliter (mg/mL), available from Sigma) at about 37° C. for about 30 minutes, 20 μl of a purified DNA solution was obtained from the incubated product by using a Qiagen DNA extraction kit (Cat 51304, QIAamp DNA Mini Kit) according to the operation protocols of the kit. In the bead beating method, after an addition of 30 mg of bare glass beads and 20 mL of the lysis solution (0.02 N NaOH solution or distilled water) to the cell pellets, the combination was vigorously vortexed using a vortexer (GENIE 2, available from Fisher Scientific) at a full velocity for about 5 minutes. After simple centrifugation, an extracted DNA solution (a lysed cell product) was recovered. In the experiment with the NLC, after an addition of distilled water alone, the cell pellets were vigorously vortexed with no glass beads present, using a vortexer (GENIE 2, available from Fisher Scientific) at a full velocity of about 3,200 rpm for about 5 minutes. Using the resulting lysed control product, PLC, and NLC as templates, a target nucleotide sequence was amplified. This amplified product was compared with a result of amplifying the target nucleotide sequence with the DNA solution extracted using the bead beating based cell lysis device used as a template. For accurate comparison, a total number of S. aureus cells injected into the chamber and a final volume of the DNA extraction solution in each control group were controlled to be consistent with those of the test sample.

4. Real-Time PCR Amplification

To lyse cells and qualify extracted DNA, real time-PCR was conducted using a GenSpector$^R$ TMC-1000 instrument (available from Samsung Electronics). A primer set (forward: 5'-GTT GCA TCG GAA ACA TTG TGT-3 (SEQ ID No. 1), reverse: 5'-ATG ACC AGC TTC GGT ACT AAA GAT-3' (SEQ ID No. 2), and GeneBank accession number AF033191) specific to the SA442 fragment of the S. aureus genome, and a primer set (forward: 5'-ACG AGT AGA TGC TCA ATA-3' (SEQ ID No. 3), reverse: 5'-GGA ATA ATG ACG CTA TGA T-3' (SEQ ID No. 4), and GeneBank accession number EF190335.1) specific to the mecA fragment of the MRSA genome were designed using a Primer3 software (Whitehead Institute/MT Center for Genome Research).

A PCR reaction mixture (about 2 μl) was prepared to have the following concentration: 0.4 μM of Taqman probe (FAM-5'-TGT ATG TAA AAG CCG TCT TG-3'-MGB-NFQ (SEQ ID No. 5) for S. aureus; and FAM-5'-CCA ATC TAA CTT CCA CAT ACC ATC T-3'-BHQ1 (SEQ ID No. 6) for MRSA), a 1× Z-Tag buffer (available from Takara Bio), 1 micromolar (μM) of each primer (available from Applied Biosystems or Sigma), 0.05 U of Z-Taq polymerase (available from Takara Bio), a 0.2 mM dNTP (available from Takara Bio), 0.5 μl of PCR-grade water (available from Ambion), and 1 μl of an extracted DNA solution. After the PCR reaction mixture was loaded into a PCR chip, thermal cycling was conducted as follows: denaturation at 95° C. for 1 minute and elongation at 60° C. for 4 seconds. The PCR conditions were designed to attain a PCR amplicon size of 72 base pairs (bp) for S. aureus and 98 bp for MRSA. The PCR amplicon sizes were further identified by gel electrophoresis (Agilent 2100 Bioanalyser, available from Agilent Technologies).

5. Experimental Results
(1) Experimental Results of Control Sample

Cell lysis and/or DNA purification effects were evaluated using a threshold cycle (Ct). Ct values of PLC samples are shown in Table 1. The Ct values in Table 1 are an average from three repeated experiments on each group.

TABLE 1

| Number of loaded S. aureus cells | Benchtop bead beating method | | Enzymatic method |
|---|---|---|---|
| (CFU) | NaOH (0.02N) | Distilled water | (lysostaphin) |
| About $10^4$ | 30.5 ± 0.35 | 34.5 ± 0.26 | 31.6 ± 0.56 |
| About $10^6$ | 23.7 ± 0.29 | 26.7 ± 0.15 | 25.7 ± 1.43 |

To improve lysis efficiency, the benchtop bead beating method was performed with a lysis solution containing a surfactant or a chemical substance. In the current example, a NaOH solution (0.02 N), known not to interfere with FOR amplification without additional purification, was used. Bead beating effects with the NaOH solution or distilled water in Table 1 indicate that NaOH, which chemically destructs cell walls, contributes to improving the DNA extraction efficiency. While not wanting to be bound by theory, regarding the enzymatic lysis of S. aureus, lysostaphin was selected because it specifically cleavages cross-linking pentaglycine bridges in the cell wall of staphylococci. The benchtop bead beating method with the NaOH solution shows a performance more than or equivalent to that of the enzyme-based DNA extraction method. Therefore, results with the used cell or virus lysis device were compared with those with the benchtop vortexing machine to evaluate efficiency. Optical density measurement is an approximate quantification of cells, which have caused variations in the Ct value of the PLC even at the same optical density with a standard deviation of about 1.5. The NLC sample vortexed with distilled water alone had a Ct value of about 31.5 at a cell concentration of $10^6$ CFU/mL.

(2) Cell Capture Results

In the present example, basic operations were as follows: (1) capturing cells on glass beads, (2) washing and drying, (3) lysing cells with in-situ bead beating, and (4) eluting the extracted DNA solution. Bacteria cells may be specifically or non-specifically captured on a solid substrate.

In addition to cell specific immunoaffinity techniques, pathogenic bacteria cells may be captured by non-specific cell capture techniques using surface thermodynamics or electrostatic interaction. In the present example, to evaluate the effect of long-range Coulombic electrostatic interactions to non-specific cell capture glass beads were modified to be positively charged on the surface. Surfaces of the glass beads were treated to have positive amine derivatives by reaction with an organosilane compound including poly(ethyleneimine) ("PEI").

After the interior of the microfluidic chamber was filled with the surface-modified glass beads, 1 mL of a sample solution containing $10^6$ CFU/mL of S. aureus cells was directed through the microfluidic chamber. Initially, results with non-modified glass beads and those with modified glass beads were compared in terms of electrostatic interaction. As a result, a Ct value of the DNA extracted with the modified glass beads was smaller by 2 than that of the DNA extracted with the non-modified glass beads, thereby indicating an increase of about 4 times in cell capture efficiency through the surface modification, considering that a difference in Ct of one (1 Ct) indicates two times the difference in initial template copy number.

To obtain quantitative data of the cell capture capacity of the cell lysis device used in the present example, after flowing through the chamber, the sample solution was recovered, centrifuged, and disrupted using a benchtop vortexing machine together with bare glass beads and an NaOH solution, as used with the PLC (hereinafter, the lysed product is referred to as "AC"). A Ct value of the AC was compared with that of a DNA solution ("AE") eluted from the bead-beating device through appropriate operations. A difference between the two values was used as a measure of cell capture efficiency and capacity of the bead beating device.

When 1 mL of each S. aureus sample solution having a different cell concentration of $10^4$, $10^5$, $10^6$, $10^7$, and $10^8$ CFU/mL was loaded, the differences between the AC and AE were maintained at about 5 or greater in the sample solutions of from $10^3$ CFU/mL to $10^7$ CFU/mL, but was reduced to about 2.5 at $10^8$ CFU/mL. Considering that one hundred times the difference in initial template copy number may induce a difference in Ct (ΔCt) of about 3.3, the capture efficiency was found to be about 90%. The manufactured bead-packed microfluidic device had a capacity of $10^7$ CFU or greater of S. aureus cells. After cell capture, the bead-packed microchamber was washed, dried with air, and then filled with the lysis solution. These results indicate that the applied cell capture method is appropriate to disrupt the captured cells by in-situ bead beating, rather than to release the captured cells. Other cell capture methods using, for example immunoaffinity, may be integrated with the cell lysis device used in the present example by employing appropriate solid surface chemistry.

(3) Effects of Liquid Volume Fraction ($f_L$) on Bead Beating Cell Lysis

Figure 9:
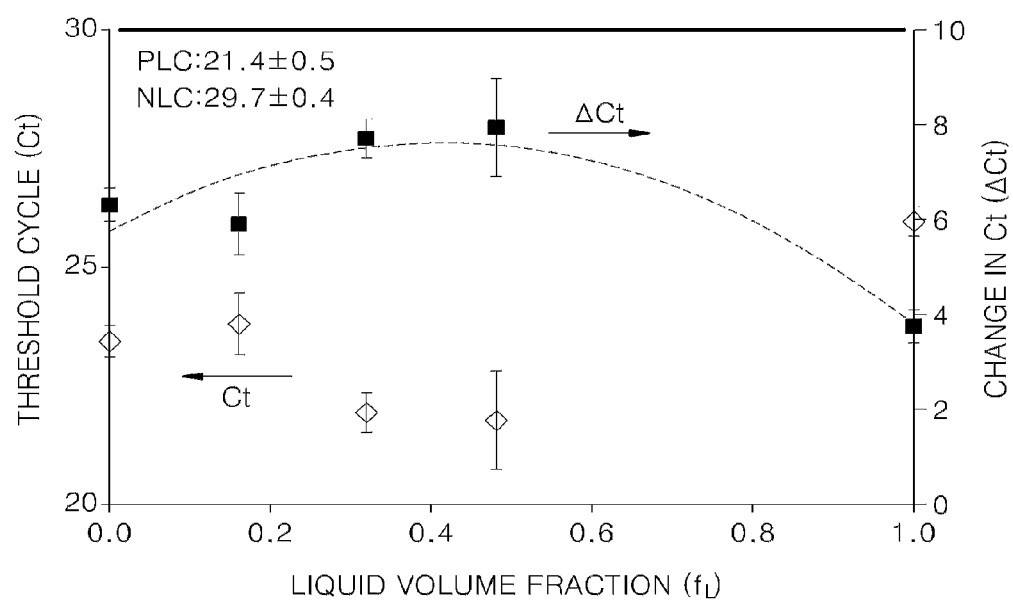
FIG. 9 is a graph of threshold cycle (Ct) and change in Ct (ΔCt) versus liquid volume fraction ($f_L$) which shows cell lysis efficiency with respect to changes in liquid volume fraction ($f_L$).

Effects of various factors on bead beating cell lysis were investigated. As a result of experiments at a membrane vibration frequency (from about 5 Hz to about 10 Hz), a membrane operating pressure (from about 20 kPa to about 80 kPa), and a depth of a pneumatic displacement chamber (from about 100 μm to about 200 μm), the factors were found not to be statistically significant on PCR Ct values. Effects of liquid viscosity on bead beating cell lysis were investigated with respect to changes in liquid volume fraction ($f_L$) during bead beating induction, the liquid volume fraction being defined by the volume of the lysis solution with respect to the pure void volume of the microfluidic chamber packed with beads. The final elution volume of DNA was adjusted to be 20 μl, by adding a NaOH solution when the extracted DNA was eluted from the chamber. FIG. 9 is a graph of threshold cycle (Ct) and change in Ct (ΔCt) versus liquid volume fraction ($f_L$) showing cell lysis efficiency with respect to changes in liquid volume fraction ($f_L$). Referring to FIG. 9, the liquid volume fraction ($f_L$) is found to correlate with cell lysis efficiency, and, while not wanting to be bound by theory, it is believed that liquid volume fraction ($f_L$) is a determining factor of cell lysis efficiency. The cell lysis efficiency was high at a liquid volume fraction ($f_L$) of 0.6 or less, and in particular, was higher at 0.5 or less, and still higher at between 0.3 and 0.5. Efficient cell lysis was also possible at a liquid volume fraction ($f_L$) of 0. This is attributed to the fact that the viscosity of the liquid solution (NaOH) is 100 times or greater than that of air, and thus, a relative amount of the liquid solution (NaOH) markedly affects the viscosity of the mixed solution (gas and liquid).

It should be understood that the exemplary embodiments disclosed herein shall be considered in a descriptive sense only and not for purposes of limitation. Descriptions of features or aspects within each embodiment should typically be considered as available for other similar features or aspects in other embodiments.

What is claimed is:

1. A method of lysing at least one of a cell and a virus, the method comprising:
   contacting a sample, which comprises at least one of a cell and a virus, with a plurality of beads which are disposed in a first chamber to obtain a combination of the sample and the beads; and
   agitating the combination of the sample and the beads to lyse the at least one of the cell and the virus,
   wherein, in the first chamber, a liquid volume fraction is 0.6 or less, and
   wherein the liquid volume fraction is a value obtained by dividing a liquid volume of the first chamber by a pure void volume equivalent to a sum of the liquid volume of the first chamber and a void volume of the first chamber,
   wherein the contacting of the sample and the beads is performed in a cell lysis device comprising
      an upper plate with a space defining the first chamber;
      a lower plate with a space defining a second chamber;
      and a flexible membrane disposed between and separating the first chamber of the upper plate and the second chamber of the lower plate;
   and wherein the method comprises pressurizing and depressurizing the second chamber by flowing a fluid into and out of the second chamber to vibrate the flexible membrane.

2. The method of claim 1, wherein the liquid volume fraction is zero, or from about 0.3 to about 0.5.

3. The method of claim 1, wherein at least one of an inlet of the first chamber and an outlet of the first chamber has a diameter which is less than a diameter of the beads.

4. The method of claim 1, wherein at least one of an inlet of the first chamber and an outlet of the first chamber has a diameter that blocks passage of the beads.

5. The method of claim 1,
   wherein at least one of a wall of the first chamber and a surface of the beads further comprises a binding material which binds to the cell or the virus, or
      the beads are capable of binding to the cell or the virus without a binding material which binds to the cell or the virus.

6. The method of claim 5, wherein the binding material comprises a specific binding material which specifically binds to the cell or virus, or a non-specific binding material which non-specifically binds to the cell or virus.

7. The method of claim 6, wherein the specific binding material comprises an antibody for an antigen, a substrate or inhibitor for an enzyme, an enzyme for a substrate, a receptor for a ligand, a ligand for a receptor, or a combination thereof.

8. The method of claim 6, wherein the non-specific binding material comprises a hydrophobic material having a water contact angle of about 70° to about 95°, or a material with at least one amino group.

9. The method of claim 1, wherein the contacting of the sample and the beads comprises flowing the sample into an inlet of the first chamber.

10. The method of claim 9, wherein the contacting of the sample and the beads further comprises discharging a portion of the sample out of an outlet of the first chamber.

11. The method of claim 1, wherein the sample comprises a liquid, and the method further comprises removing at least a portion of the liquid in the first chamber to reduce the liquid volume before the agitating and after the contacting of the sample and the beads.

12. The method of claim 11, wherein the removing of at least a portion of the liquid volume comprises drying an interior of the first chamber.

13. The method of claim 12, wherein the drying comprises flowing a gas into the first chamber, or heating the first chamber.

14. The method of claim 5, further comprising washing the wall of the first chamber or the surface of the beads after the contacting of the sample and the beads.

15. The method of claim 1, further comprising introducing a cell or virus lysis solution into the first chamber.

16. The method of claim 15, wherein the agitating is performed after the step of introducing of the cell or virus lysis solution.

17. The method of claim 1, wherein the vibrating vibrates a flexible membrane at a frequency of from about 0.001 Hertz to about 100 kiloHertz.

18. The method of claim 1, wherein the method is performed using a cell lysis device comprising:
   a first chamber fluidly connected to an inlet and an outlet, and a plurality of beads disposed in the first chamber, wherein a diameter of the beads is larger than a diameter of the inlet and the outlet;
   a second chamber comprising a port fluidly connected to the second chamber; and
   a flexible membrane sealably disposed between the first and second chambers.

19. The method of claim 1, wherein increasing pressure within the second chamber reduces the volume of the first chamber.

* * * * *